US008437540B2

(12) United States Patent
Stephan et al.

(10) Patent No.: US 8,437,540 B2
(45) Date of Patent: May 7, 2013

(54) METHOD AND APPARATUS FOR CHARACTERIZING PIGMENT SPOTS

(75) Inventors: Sandrine Stephan, Beaugency (FR); Delphine Pelle de Queral, Ingre (FR)

(73) Assignee: LVMH Recherche, Saint Jean de Braye (FR)

(*) Notice: Subject to any disclaimer, the term of this patent is extended or adjusted under 35 U.S.C. 154(b) by 468 days.

(21) Appl. No.: 12/763,656

(22) Filed: Apr. 20, 2010

(65) Prior Publication Data
US 2010/0272333 A1 Oct. 28, 2010

(30) Foreign Application Priority Data

Apr. 23, 2009 (FR) ...................................... 09 52662

(51) Int. Cl.
*G06K 9/00* (2006.01)
*G06K 9/40* (2006.01)

(52) U.S. Cl.
USPC .......................................... 382/162; 382/260

(58) Field of Classification Search .................. 382/118, 382/128, 162, 164, 165, 169, 260
See application file for complete search history.

(56) References Cited

U.S. PATENT DOCUMENTS

| | | | |
|---|---|---|---|
| 6,551,982 B1 | 4/2003 | Ricci et al. | |
| 2003/0063801 A1* | 4/2003 | Rubinstenn et al. | 382/190 |
| 2007/0086651 A1* | 4/2007 | Stephan et al. | 382/162 |

FOREIGN PATENT DOCUMENTS

| | | |
|---|---|---|
| FR | 2 891 641 A1 | 4/2007 |
| WO | WO 00/67398 | 11/2000 |
| WO | WO 2007/042708 A1 | 4/2007 |

OTHER PUBLICATIONS

Chang et al., "A systematic heuristic approach for feature selection for melanoma discrimination using clinical images," *Skin Research and Technology* (2005) 11: 165-178. XP002573511.
Ganster et al., "Automated melanoma recognition," *IEEE Transactions on Medical Imaging* (2001) 20 (3): 233-239. XP001096769.
Sikorski, J., "Identification of malignant melanoma by wavelet analysis," *Proceedings of Student/Faculty Research Day, CSIS, Place University* (2004): 10.1-10.9. XP002573510.
Mehrübeoğlu et al., "Skin lesion classification using oblique-incidence diffuse reflectance spectroscopic imaging," *Applied Optics* (2002) 41 (1): 182-192. XP002573512.
French Search Report mailed on Mar. 18, 2010 for priority French application FR 0952662.

* cited by examiner

*Primary Examiner* — Daniel Mariam
(74) *Attorney, Agent, or Firm* — Merchant & Gould P.C.

(57) ABSTRACT

A method involving filters of an extracted plane from a digital image of an area of skin to obtain a first ripple image and a second roughness image, from which appropriate computation devices are used to calculate different types of gray levels to characterize a pigment spot, notably with regard to the uniformity or disparity of the spot. A method measures the effectiveness of a cutaneous pigment spot treatment by an active pigmenting or depigmenting agent.

21 Claims, 2 Drawing Sheets

METHOD AND APPARATUS FOR CHARACTERIZING PIGMENT SPOTS

BACKGROUND OF THE INVENTION

The invention relates to a method and apparatus for characterizing pigment spots, and its application in a method of assessing the pigmenting or depigmenting effect of a cosmetic, dermatological or pharmaceutical product.

STATE OF THE ART

The document U.S. Pat. No. 6,551,982 B1 discloses a method and a device for the non-invasive estimating of a relative age of a person based on a near-infrared method, called NIR method, that uses a wavelength in the 700 to 2500 nanometer range.

Also, the document WO 00/67398 A1 discloses imaging systems and methods for analyzing the skin that implement the acquisition and creation of various digital images in order to view skin defects, and then take into account a sub-image containing the skin defect.

Also, the document WO 2007/042 708, filed by the Applicant, discloses a method and apparatus for characterizing skin imperfections and a method of assessing the anti-aging effect of a cosmetic product.

AIMS OF THE INVENTION

The aim of the present invention is to resolve the technical problem that involves providing a novel method and a novel apparatus for characterizing skin pigment spots that is capable of providing a greater accuracy in the characterization of the pigment imperfections, both over wide spatial variations and small spatial variations of the pigmentation levels, and do so even within or in the vicinity of the pigment spot, that are relatively easy to implement, safe and reliable with respect to the result obtained.

Another aim of the present invention is to resolve the technical problem that involves providing a method of assessing the pigmenting or depigmenting effect of a cosmetic, dermatological or pharmaceutical product, that implements the method or the apparatus for characterizing skin pigment spots.

The present invention provides a satisfactory solution to both of these technical problems.

SUMMARY OF THE INVENTION

Definitions

The expression "gray level" should be understood to mean the quantization of the light intensity picked up on a pixel of the digital sensor of the digital color image-taking device.

The term "filtering" should be understood to mean a mathematical processing operation applied to all or part of a digital image to modify or enhance its appearance and thus obtain a new "filtered" image, the aim of said mathematical processing operation being to modify the value of the pixels of an image. Depending on the filter used, the new value of a given pixel may be calculated by taking into account all of the pixels of the initial image, or even by taking into account only a vicinity of the corresponding pixel in the original image.

The expression "thresholding of the gray levels" should be understood to mean the elimination of the gray levels below a certain predetermined gray level threshold, in order to eliminate parasitic elements or artifacts.

The expression "wide spatial variations of the grey levels" should be understood to mean the extreme differences of the grey levels on a large number of pixels corresponding to a large surface of the considered extracted image.

The expression "small spatial variations of the grey levels" should be understood to mean the small differences of the grey levels on a small number of pixels corresponding to a small surface of the considered extracted image.

The expression "representative group" should be understood to mean a group of people representative of a population of given age, and that can be used to establish meaningful statistical results concerning the effectiveness of a treatment agent or product, in the context of the implementation of the invention.

According to a first aspect, the present invention provides a method of characterizing skin pigment spots, in which:
   a) at least one digital color image is taken, using a digital color image-taking device, of at least one determined area of skin including at least a portion of a pigment spot, said image being defined by a multiplicity of pixels, said image being transmitted to a digital image processing device;
   b) the duly stored digital image is divided up into three color planes: red, green, blue, called R, G, B, using said image processing device;
   c) just one of these planes, or a combination of these planes, is extracted; said method being characterized in that:
   d) at least a portion of the extracted plane is filtered to obtain a first sub-image called ripple image and a second sub-image called roughness image;
   e) appropriate computation means are used to calculate, over at least a portion of the ripple image and/or a portion of the roughness image, at least one parameter from:
      the arithmetic mean of the mean deviations of the gray levels;
      the root mean square of the mean deviations of the gray levels;
      the difference between the lowest gray level and the highest gray level;
      the difference between the highest gray level and the average of the gray levels; and
      finally the difference between the lowest gray level and the average of the gray levels;
   to characterize said pigment spot, notably with regard to the uniformity or disparity of the spot.

The ripple image, as represented in FIG. 2 of this application, characterizes the wide spatial variations of the gray levels measured for each pixel of a plane extracted from the digital color image of the pigment spot, or of a combination of these planes. The ripple image is representative of the wide spatial pigmentation variations for the spot being studied.

The roughness image, as represented in FIG. 3 of this application, characterizes the small spatial variations of the gray levels measured from the same plane or the same combination of planes. The roughness image is representative of spatial pigmentation variations for small objects within the spot being studied.

Each of the sub-images is obtained using a filtering tool like those usually included in image analysis software. Typical of such software is the VISILOG® image analysis software from EOTECH, France, which contains such filters.

According to the invention, a plane, or a combination of planes, extracted from the original image, is filtered for example using a median filter, to obtain a "smoothed" image, corresponding to the ripple image.

Then, using the image software, the ripple sub-image is subtracted from the plane of the original image, to obtain the roughness sub-image.

According to a particular embodiment of this method, said method is characterized in that the pigment spot is a cutaneous dyschromia taking the form of at least one spot of color different from the healthy skin because of an abnormal pigmentation, resulting notably from the cutaneous effects of photo-dermatoses, from the pigmentation induced by contact dermatoses or medicinal photo-dermatoses, or even by melasma, keratoses, senile or actinic for example, senile lentigo (aging spots), solar lentigo, the persistent effects of burns, such as sunburns and other skin wounds, or scars, spots due to allergic or phototoxic reactions, dermatitis or other similar small fixed pigmented lesions; or depigmented areas induced by certain leukodermas such as vitiligo.

According to a particular embodiment of the method according to the invention, said method is characterized in that at least a portion of the pigment spot is detected in the extracted plane or in at least one of the extracted sub-images; and these calculations are applied to said pigment spot.

According to another particular embodiment of the method according to the invention, said method is characterized in that characterizing the spot includes measuring parameters situated on the edge of or outside the pigment spot in the vicinity of the edge of the spot, from the extracted plane or the above-mentioned sub-images.

According to another particular embodiment of the method according to the invention, said method is characterized in that the blue color plane is extracted.

According to another particular embodiment of the method according to the invention, said method is characterized in that said image is enlarged enabling an operator to better view the skin imperfections and assess the thresholding of the gray levels with which to eliminate the parasitic elements or artifacts.

According to yet another particular embodiment of the method according to the invention, said method is characterized in that either a digital color photo apparatus or a digital color camera of MONO-CCD, DI-CCD or TRI-CCD type, for example the Fotofinder™ camera from DEKA that has an image resolution of 450 000 pixels with 4 V LED built-in lighting, or a color camera available on the market, notably from SONY, is used as the digital color image-taking device.

According to an advantageous embodiment of the method according to the invention, said method is characterized in that means of lighting the skin surface for which the digital image is taken are provided.

According to another particular embodiment of the method according to the invention, said method is characterized in that at least one image or a plurality of images of the skin of one and the same person are stored on a digital data storage device.

According to a second aspect, the present invention provides an apparatus for characterizing a person's skin pigment spots, comprising:
  a) a digital color image-taking device for taking at least one digital color image of at least one determined area of skin, said image being defined by a multiplicity of pixels, that is transmitted to a digital image processing device;
  b) means of dividing up the digital image into three color planes: red, green, blue, called R, G, B, using said image processing device;
  c) means of extracting just one of these planes or a combination of these planes;

said apparatus being characterized in that it comprises:
  d) appropriate means of calculating, over at least a portion of the ripple image and/or a portion of the roughness image, at least one parameter chosen from:
    the arithmetic mean of the mean deviations of the gray levels;
    the root mean square of the mean deviations of the gray levels;
    the difference between the lowest gray level and the highest gray level;
    the difference between the highest gray level and the average of the gray levels; and
    finally the difference between the lowest gray level and the average of the gray levels;
  to characterize said pigment spot, notably with regard to the uniformity or disparity of the spot.

According to a particular embodiment of the apparatus according to the invention, said apparatus is characterized in that the extraction means extract the blue color plane on which the computation means perform the abovementioned calculation of at least one abovementioned parameter.

According to another particular embodiment of the apparatus according to the invention, said apparatus is characterized in that it comprises means of taking into account a thresholding of the gray levels, that is to say means for eliminating the gray levels below a certain predetermined gray level threshold, in order to eliminate parasitic elements or artifacts.

According to another particular embodiment of the apparatus according to the invention, said apparatus is characterized in that it comprises means for extracting from said digital image a limited surface area of the skin of the person to be analyzed, on which the computation means proceed to analyze the pigment spots over all of this limited surface area, and notably to calculate said parameters and perform said thresholding.

According to another particular embodiment of the apparatus according to the invention, said apparatus is characterized in that said limited surface area is an area selected from said digital image.

According to another particular embodiment of the apparatus according to the invention, said apparatus is characterized in that it comprises means of enlarging said image obtained by the digital color image-taking device enabling an operator to better view the pigment spots and assess the thresholding of the gray levels with which to eliminate the parasitic elements or artifacts.

According to another particular embodiment of the apparatus according to the invention, said apparatus is characterized in that either a digital color photo apparatus or a digital color camera is used as the digital color image-taking device.

According to yet another particular embodiment of the apparatus according to the invention, said apparatus is characterized in that it comprises means of storing at least one image or a plurality of images of the skin of one and the same person, notably over a number of different areas, on a digital data storage device.

According to another particular embodiment of the apparatus according to the invention, this apparatus is characterized in that it comprises means of lighting the skin surface for which the digital image is taken.

According to another particular embodiment of the apparatus according to the invention, said apparatus is characterized in that it comprises a computer combined with a monitor comprising a screen, a keyboard and a mouse and comprising software incorporating all the abovementioned means, including:

means of enlarging said image;

means of storing at least one image or a plurality of images of the skin;

means of dividing up the digital image into three color planes: red, green, blue, called R, G, B;

means of extracting just one of these planes; preferentially the so-called blue plane corresponding to the blue color;

means of calculating, over at least a portion of the ripple image and/or a portion of the roughness image, at least one parameter selected from:

the arithmetic mean of the mean deviations of the gray levels;

the root mean square of the mean deviations of the gray levels;

the difference between the lowest gray level and the highest gray level;

the difference between the highest gray level and the average of the gray levels;

the difference between the lowest gray level and the average of the gray levels;

means of taking into account a thresholding of the gray levels;

for characterizing said pigment spot, notably with regard to the uniformity or disparity of the spot.

According to another particular embodiment of the apparatus according to the invention, said apparatus is characterized in that the computation means take into account the average of each parameter.

According to a third aspect, the invention also covers a method of measuring the effectiveness of a cutaneous pigment spot treatment by an active pigmenting or depigmenting cosmetic, dermatological or pharmaceutical agent or a cosmetic, dermatological or pharmaceutical composition including such an active pigmenting or depigmenting agent, comprising:

a) the characterization of at least one spot according to the above-mentioned method;

b) the characterization of said spot according to the above-mentioned method, after having performed a cosmetic, dermatological or therapeutic treatment of at least said spot using said active agent or said composition;

c) the two characterizations are compared with each other to determine the effectiveness of said treatment.

According to a particular embodiment of this method, said method is characterized in that characterizing the spot includes measuring parameters situated on the edge of or outside the pigment spot in the vicinity of the edge of the spot.

According to a particular embodiment of this method, said method is characterized in that the blue color plane, on which the abovementioned parameterizing of at least one abovementioned parameter is carried out, is extracted.

According to another particular embodiment of this method, said method is also characterized in that a thresholding of the gray levels is carried out in order to determine the edge of the pigment spot.

According to this embodiment, it is also possible to determine a particular area, called "crown" in this application, the inner and outer outlines of which, either side of the above-mentioned edge of said pigment spot, are plotted at a distance defined by the user corresponding to a chosen number of pixels.

Other particular characteristics of this method will become clearly apparent to those skilled in the art from the description of the abovementioned method of characterizing skin pigment spots.

By virtue of the methods and the apparatus according to the invention, the previously stated technical problems are resolved in a simple, safe and reliable manner.

Other aims, characteristics and benefits of the invention will become clearly apparent in light of the following explanatory description given with reference to a currently preferred embodiment of the invention.

DETAILED DESCRIPTION

Figure 1:
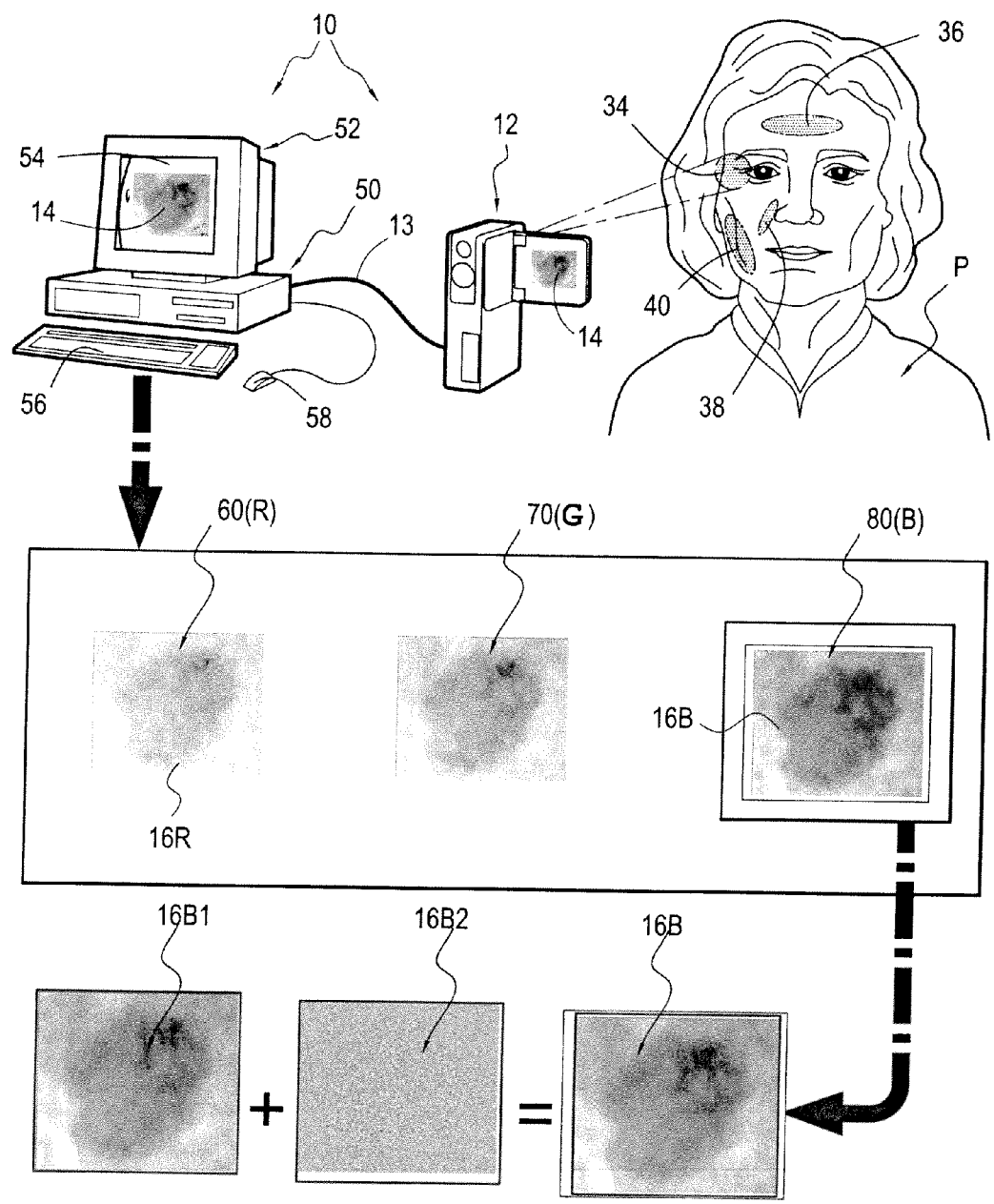
FIG. 1 represents an apparatus for characterizing a person's skin pigment spots, for implementing the method of characterizing skin pigment spots described previously.

Referring to FIG. 1, a currently preferred embodiment of a rig according to the invention is represented by the general reference numeral 10. To ensure positioning accuracy for the person P, said person will be seated on a repositioning table, for example available on the market under the trade name VISIOFACE, from the company EOTECH in France.

This apparatus 10 is designed to characterize a person's pigment spots.

According to a particular embodiment of the apparatus according to the invention, it is possible to provide a device 12 for taking digital color images 14 of at least one determined area of skin 34, 36, 38, 40, said image 14 being defined by a multiplicity of pixels.

The device 12 may be, for example:

either a digital color photo apparatus of good resolution available on the market;

or a digital color camera 12 such as the Fotofinder™ camera from the company DEKA that has an image resolution of 450 000 pixels with 4 V LED built-in lighting, or a digital color camera available on the market notably from Sony.

This digital image is then transmitted, according to well known transfer means available on the market, such as a wire 13, to the digital image processing device.

According to a particular variant embodiment, said image-taking device 12 can be used to take an image of a surface of the skin.

Also, as is well known to those skilled in the art, such a digital image processing device is available on the market, for example, in software form, such as the image analysis software VISILOG v. 6.6, that can be installed on a computer 50 linked to said camera 12 by an appropriate lead 13. Said computer 50 is naturally combined with a monitor 52 with its screen 54, its keyboard 56 and a mouse 58.

According to the invention, the digital image processing device comprises means of dividing up the digital image into three color planes: red 60, green 70, blue 80, called R, G, B; the digital image processing device also comprises means of extracting just one of these planes or a combination of these planes; in this case, provision is made, for the pigment spots 16, to extract the so-called blue plane 80, corresponding to the blue color, and the so-called blue pigment spot obtained is thus sub-referenced 16B.

It has been discovered according to the invention that the blue plane 80 is preferred because it offers the greatest contrast and makes it possible to better view the pigment spots.

According to the invention, the apparatus also notably comprises computation means, in this case provided in said software, appropriate means of calculating, over at least a portion of the ripple image and/or a portion of the roughness image, at least one parameter chosen from:

the arithmetic mean of the mean deviations of the gray levels;

the root mean square of the mean deviations of the gray levels;

the difference between the lowest gray level and the highest gray level;

the difference between the highest gray level and the average of the gray levels; and finally the difference between the lowest gray level and the average of the gray levels;

to characterize said pigment spot, notably with regard to the uniformity or disparity of the spot.

A mathematical filter provided in the image analysis software can be applied, to the extracted blue plane 80, to eliminate the parasitic noise from the image, such as reflection.

According to yet another particular embodiment of this apparatus, said apparatus is characterized in that provision is made to take said image of a limited surface area 34, 36, 38, 40 of the skin of the person P to be analyzed, on which the computation means proceed to analyze skin imperfections over the whole of this surface area.

According to another particular embodiment, there are provided means (not represented here) of lighting the skin surface for which the digital image is taken.

According to a particular embodiment of the apparatus according to the invention, said apparatus comprises storage means, incorporated in the software, for at least one image or a plurality of images of the skin of one and the same person on a device for storing digital data incorporated in the software.

According to another particular embodiment of the apparatus according to the invention, said apparatus is characterized in that the computation means take into account the average of each parameter.

According to another advantageous characteristic of the apparatus according to the invention, said apparatus comprises means of taking into account a thresholding of the gray levels, also incorporated in the software, that is to say means for eliminating the gray levels below a certain predetermined gray level threshold, in order to eliminate parasitic elements, thus producing an image 80' stripped of the parasitic elements.

There is also advantageously provided a second mathematical filtering, also provided in the software, in order to eliminate the minimum areas detected in the preceding thresholding step and that do not present any interest, here obtaining an image 80B on which the pigment spots appear very clearly. It is on this last image 80B that the image analysis and calculation steps will preferentially be carried out, as indicated hereinbelow.

First of all, each digital image is approached in a profilometric manner.

For this, by virtue of the abovementioned digital color image-taking device 12, and in particular from the image of the blue color plane 80(B), the gray level profilometry parameters are calculated over different portions of the image.

Figure 2:
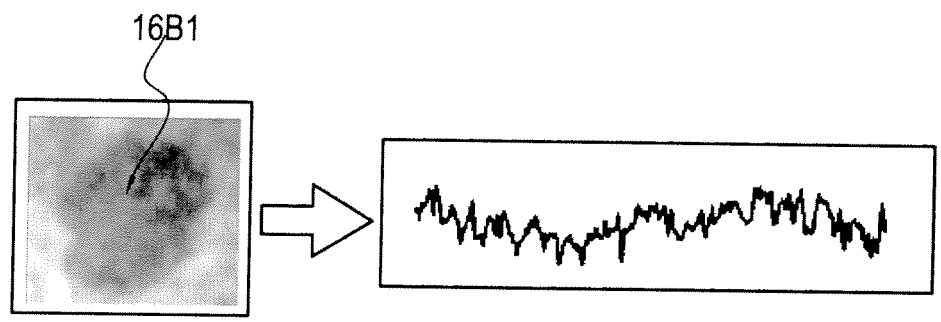
FIG. 2 represents a sub-image of the spot, called ripple image, which characterizes the wide spatial variations of the gray levels.
Figure 3:
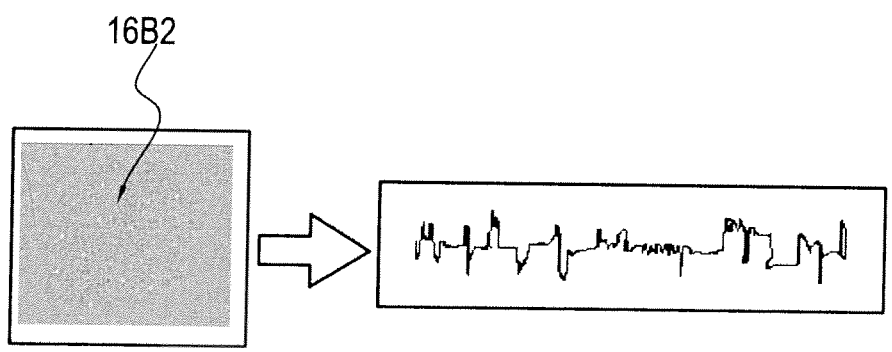
FIG. 3 represents a sub-image of the spot, called roughness image, which characterizes the small spatial variations of the gray levels.

For this, the image 80(B), and in particular the image of the pigment spot 16B, is subdivided:

into a first sub-image, called ripple image 16B1, which can be seen in FIG. 1 and appears in FIG. 2, representative of the wide spatial variations of the gray levels, as shown by the ripple curve;

into a second sub-image, called roughness image 16B2, which can be seen in FIG. 1 and appears in FIG. 3, representative of the small spatial variations of the gray levels, as shown by the roughness curve.

In these two sub-images, the following parameters are calculated:

Sa: the arithmetic mean of the mean deviations, or $$Sa = \frac{1}{NM} \sum_{x=0}^{N-1} \sum_{y=0}^{M-1} |z_{xy}|$$

Sq: the root mean square of the mean deviations, or $$Sq = \sqrt{\frac{1}{NM} \sum_{x=0}^{N-1} \sum_{y=0}^{M-1} z_{x,y}^2}$$

St: the total height of the surface; St=height between the highest peak and the deepest hollow;

Sp: the height of the highest projection from the surface; height between the highest peak and the median plane;

Sv: depth of the deepest valley of the surface; depth between the median plane and the deepest valley.

These parameters are linked to the variations of the amplitudes of the gray levels, and characterize the uniformity of the images being studied.

By virtue of the built-in software, the application calculates the parameters:

SaT, SqT, StT, SpT, SvT: parameters calculated over the spot area of the ripple image;

SaR, SqR, StR, SpR, SvR: parameters calculated over the spot area of the roughness image;

StC, SpC, SvC: parameters calculated over the crown of the spot.

A calculation of the contrast is also carried out by calculating the brightness of the spot and of the adjacent skin.

LumP: skin brightness parameter

LumT: spot brightness parameter contrast=LumP−LumT/LumP

The pigment spots are then quantized as indicated in example 2 hereinbelow.

Example 2 According to the Invention

Quantization of the Imperfections: Example of Pigment Spots

For this, a sample of 15 volunteers, men and/or women, statistically representative for their pigment spots on the hands, is selected.

A spot image bank is created, said spot images having been rated internally by an esthetician and the inventor respectively as spots that are not very visible, visible or highly visible, and the plates of 9 images taken in each category are respectively the subject of FIGS. 6, 7 and 8.

The summary of the results is given in table I hereinbelow.

TABLE I

|   |   | $1P_{(n=22)}$ | $2V_{(n=39)}$ | $3T_{(n=27)}$ | $P_{class}$ |
|---|---|---|---|---|---|
| T | SaT | $8.0^A$ | $9.9^B$ | $10.5^B$ | $S_{(p<0.01)}$ |
|   | SqT | $9.7^A$ | $12.0^B$ | $12.6^B$ | $S_{(p<0.01)}$ |
|   | SsT | $46.6^A$ | $57.2^B$ | $68.0^C$ | $S_{(p<0.01)}$ |
|   | SpT | $26.7^A$ | $31.4^B$ | $43.0^C$ | $S_{(p<0.01)}$ |
|   | SvT | $20.0^A$ | $23.0^{AB}$ | $25.0^B$ | $S_{(p=0.05)}$ |
| C | StC | $66.0^A$ | $87.6^B$ | $101.5^C$ | $S_{(p<0.01)}$ |
|   | SpC | $33.3^A$ | $40.8^B$ | $50.2^C$ | $S_{(p<0.01)}$ |
|   | SvC | $32.8^A$ | $43.9^B$ | $51.3^C$ | $S_{(p<0.01)}$ |
| R | SaR | $3.6^A$ | $4.3^B$ | $4.3^B$ | $S_{(p<0.01)}$ |
|   | SqR | $4.8^A$ | $5.9^B$ | $5.7^B$ | $S_{(p<0.01)}$ |
|   | StR | $56.7^A$ | $72.3^B$ | $68.8^{AB}$ | $S_{(p=0.04)}$ |
|   | SpR | $29.9^A$ | $41.3^B$ | $37.5^{AB}$ | $S_{(p=0.05)}$ |
|   | SvR | $24.1^A$ | $31.0^B$ | $31.3^B$ | $S_{(p<0.01)}$ |
| (LumP − LumT) |   | $25.1^A$ | $36.3^B$ | $41.9^C$ | $S_{(p<0.01)}$ |

T: ripple image of the spot area
C: image of the crown (area either side of the edge of the spot then containing a spot portion and a non-spot portion)
R: roughness image of the spot area The meanings of the abbreviations are as given in example 1 hereinabove:

The conclusions resulting from this table 1, based on the analysis of the variant with 5% risk, are as follows:

The parameters studied make it possible to clearly discriminate the different classes of pigment spots defined visually:

For the parameters SsT, SpT, StC, SpC, SvC, (LumP−LumT), a significant difference is observed between each of the three classes of spots.

For the parameters SaT, SqT, SaR, SqR, SpR, SvR, a significant difference is observed between the class of spots classified P (not very visible) on the one hand and those of spots classified V (visible) and T (highly visible). However, no significant difference is observed between the classes V and T.

By virtue of the apparatus according to the invention, it is possible to implement the creation of a calibration curve for the degree of pigmentation as indicated in example 2, which can be used to determine the degree of pigmentation of the skin of a person which can then be used to implement a test to assess the effectiveness of a pigmenting or depigmenting cosmetic, dermatological or pharmaceutical product.

Example 3 of the Invention

Test for Assessing the Effectiveness of a Depigmenting Cosmetic Product

The images acquired during an effectiveness test performed for an anti-spot product are analyzed.

The anti-spot product is a night cream in the form of an oil-in-water emulsion, comprising 3.3% by weight of magnesium ascorbyl phosphate (source: Showa Denko) which is an agent that has skin lightening properties.

The test modalities are as follows:
number of volunteers: 14 volunteers, 17 spots studied
area: hand
application of the composition: 4 product applications, applied topically (0.560 ml), once a day
use, as many times as necessary, of a cream for the hands, with a solar protection index (SPF 20)
measurement time: before the start of the study (T1), then after 6 weeks of treatment
apparatus: Fotofinder, from DEKA, image-taking device: ¼" CCD (total: 470 000 pixels), built-in lighting: LED, 4 volts.

For each criterion, the following statistical analyses are carried out for a 5% risk:
overall analysis of the variance
variance analysis for the comparison before treatment and 6 weeks after treatment
overall analysis of the variance by removing the volunteers with excessive residues. The residues are aberrant values or values that increase the background noise of the analysis.

Results

Parameters calculated on the ripple sub-image of the pigment spot (large non-uniformities in the gray levels): SaT SqT StT SpT drop significantly. Only SvT does not vary significantly.

Parameters calculated on the ripple sub-image of the crown of the spot: StC SpC SvC do not vary significantly.

Parameters calculated on the roughness sub-image of the pigment spot (small non-uniformities in the gray levels): SaR SqR drop significantly. StR SpR SvR do not vary significantly.

Brightness and contrast parameters: LumT, LumP drop significantly. Contrast drops significantly.

These results reflect a lightening of the spot area and of the area of skin adjacent to the spot. The spot exhibits significantly less contrast after 6 weeks of treatment.

A significant reduction of most of the parameters obtained from the ripple sub-image is observed, which characterizes the large non-uniformities of tone of the spot area and of the adjacent area of skin.

This confirms the effectiveness of the agent tested as a depigmenting agent.

The invention also covers all the means that constitute technical equivalents of the means described, and their various combinations.

The invention claimed is:

1. A method for characterizing skin pigment spots, comprising:
   a) taking at least one digital color image, using a digital color image-taking device, of at least one determined area of skin including at least a portion of a pigment spot, said image being defined by a multiplicity of pixels, said image being transmitted to a digital image processing device to be stored;
   b) dividing the stored digital image into three color planes: red, green, blue, called R, G, B, using said image processing device;
   c) extracting just one of these planes, or a combination of these planes;
   d) filtering at least a portion of the extracted plane to obtain a first sub-image designated a ripple image characterizing wide spatial variations of gray levels for each pixel of said extracted image and a second sub-image designated a roughness image characterizing small spatial variations of the gray levels for each pixel of said extracted image;
   e) using appropriate computation means to calculate, over at least a portion of at least the ripple image, and of at least a portion of the roughness image, at least one parameter from: the arithmetic mean of the mean deviations of the gray levels; the root mean square of the mean deviations of the gray levels; the difference between the lowest gray level and the highest gray level; the difference between the highest gray level and the average of the gray levels; and the difference between the lowest gray level and the average of the gray levels;
   characterizing said pigment spot with regard to the uniformity or disparity of the spot.

2. The method of claim 1, wherein the pigment spot is selected from the group: a cutaneous dyschromia taking the form of at least one spot of color different from the healthy skin because of an abnormal pigmentation, a photo-dermatose, a melasma, keratoses, a senile lentigo, an aging spot, a solar lentigo, a persistent effect of burns, a skin wound, a scar, a spot due to allergic or phototoxic reactions, a dermatitis a pigmented lesions; a depigmented area, a leukodermas, and vitiligo.

3. The method of claim 1, wherein at least a portion of the pigment spot is detected in the extracted plane or in at least one of the extracted sub-images; and calculations of said at least one parameter are applied to said pigment spot.

4. The method of claim 3, wherein characterizing the spot includes measuring parameters from a location selected from the edge, from outside the pigment spot in the vicinity of the edge of the spot, from the extracted plane or the sub-images.

5. The method of claim 1, further comprising extracting the blue color plane.

6. The method of claim 1, wherein said image is enlarged enabling an operator to better view the skin imperfections and assess the thresholding of the gray levels with which to eliminate parasitic elements or artifacts.

7. The method of claim 1, wherein the digital color image-taking device is selected from a digital color photo apparatus and a digital color camera.

8. The method of claim 1, comprising storing one image or a plurality of images of the skin of one and the same person over several different areas, on the digital data processing device.

9. The method of claim 1, wherein the computation means take into account the average of each parameter.

10. A method of measuring the effectiveness of a cutaneous pigment spot treatment by an active pigmenting or depigmenting cosmetic, dermatological or pharmaceutical agent or a cosmetic, dermatological or pharmaceutical composition including such an active agent, comprising:
   a) characterizing at least one spot according to the method of claim 1;
   b) characterizing said spot according to the method of claim 1, after having performed a cosmetic, dermatological or therapeutic treatment of at least said spot using said active agent or said composition;
   c) comparing the two characterizations to determine the effectiveness of said treatment.

11. The method of claim 10, wherein the pigment spot is selected from the group: a cutaneous dyschromia taking the form of at least one spot of color different from the healthy skin because of an abnormal pigmentation, a photo-dermatose, a melasma, keratoses, a senile lentigo, an aging spot, a solar lentigo, a persistent effect of burns, a skin wound, a scar, a spot due to allergic or phototoxic reactions, a dermatitis, a pigmented lesion; a depigmented area, a leukodermas, and vitiligo.

12. The method of claim 10, wherein characterizing the spot comprises measuring parameters located on a location selected from the edge of the spot, and the outside of the pigment spot in the vicinity of the edge of the spot.

13. An apparatus for characterizing a person's skin pigment spots, comprising:
   a) a digital color image-taking device for taking at least one digital color image of at least one determined area of skin, said image being defined by a multiplicity of pixels, transmitted to a digital image processing device to be stored;
   b) means for dividing up the digital image into three color planes: red, green, blue, called R, G, B, using said image processing device;
   c) means for extracting just one of the planes or a combination of the planes;
   d) computation means for calculating, over at least a portion of at least one of a ripple image characterizing wide spatial variations of gray levels for each pixel of said extracted image, and of at least a portion of a roughness image characterizing small spatial variations of the gray levels for each pixel of said extracted image, at least one parameter chosen from: the arithmetic mean of the mean deviations of the gray levels; the root mean square of the mean deviations of the gray levels; the difference between the lowest gray level and the highest gray level; the difference between the highest gray level and the average of the gray levels; and finally the difference between the lowest gray level and the average of the gray levels;
   to characterize said pigment spot with regard to the uniformity or disparity of the spot.

14. The apparatus of claim 13, wherein the extraction means extract the blue color plane on which the computation means perform calculation of the at least one parameter.

15. The apparatus of claim 13, comprising thresholding means for thresholding of the gray levels, to eliminate the gray levels below a certain predetermined gray level threshold, in order to eliminate parasitic elements or artifacts.

16. The apparatus of claim 15, further comprising means for extracting from said digital image a limited surface area of the skin of the person to be analyzed, on which the computation means proceed to analyze the pigment spots over all of the limited surface area, to calculate said at least one parameter and perform said thresholding.

17. The apparatus of claim 13, comprising means for enlarging said image obtained by the digital color image-taking device enabling an operator to better view the pigment spots and assess the thresholding of the gray levels with which to eliminate the parasitic elements or artifacts.

18. The apparatus of claim 13, wherein the digital color image-taking device is selected from a digital color photo apparatus and a digital color camera.

19. The apparatus of claim 13, wherein the processing means are storing one image or a plurality of images of the skin of one and the same person on the digital data storage device.

20. The apparatus of claim 13, comprising a computer combined with a monitor comprising a screen, a keyboard and a mouse and comprising software incorporating all the means, including:
   means for enlarging said image;
   means for storing at least one image or a plurality of images of the skin;
   means for dividing up the digital image into three color planes: red, green, blue, called R, G, B;
   means for extracting just one of the planes; —means for calculating, over at least a portion of the ripple image and/or a portion of the roughness image, at least one parameter selected from: the arithmetic mean of the mean deviations of the gray levels; the root mean square of the mean deviations of the gray levels; the difference between the lowest gray level and the highest gray level; the difference between the highest gray level and the average of the gray levels; the difference between the lowest gray level and the average of the gray levels; means for taking into account a thresholding of the gray levels;

for characterizing said pigment spot, with regard to the uniformity or disparity of the spot.

21. The apparatus of claim 13, comprising extracting the blue plane corresponding to the blue color.

* * * * *